United States Patent
Ante et al.

(10) Patent No.: US 8,490,465 B2
(45) Date of Patent: Jul. 23, 2013

(54) METHOD FOR THE ON-BOARD FUNCTIONAL DIAGNOSIS OF A SOOT SENSOR IN A MOTOR VEHICLE AND/OR FOR THE DETECTION OF FURTHER CONSTITUENTS IN THE SOOT

(75) Inventors: Johannes Ante, Regensburg (DE); Rudolf Bierl, Regensburg (DE); Markus Herrmann, Regensburg (DE); Andreas Ott, Steinsberg (DE); Willibald Reitmeier, Hohenschambach (DE); Denny Schaedlich, Neustadt (DE); Manfred Weigl, Viehhausen (DE); Andreas Wildgen, Nittendorf (DE)

(73) Assignee: Continental Automotive GmbH, Hannover (DE)

( * ) Notice: Subject to any disclaimer, the term of this patent is extended or adjusted under 35 U.S.C. 154(b) by 395 days.

(21) Appl. No.: 12/836,118

(22) Filed: Jul. 14, 2010

(65) Prior Publication Data

US 2011/0011154 A1    Jan. 20, 2011

(30) Foreign Application Priority Data

Jul. 14, 2009    (DE) .......................... 10 2009 033 231

(51) Int. Cl.
*G01N 25/00*    (2006.01)
(52) U.S. Cl.
USPC .......................................................... 73/23.2
(58) Field of Classification Search
USPC .......................................................... 73/23.2
See application file for complete search history.

(56) References Cited

U.S. PATENT DOCUMENTS

| | | | | |
|---|---|---|---|---|
| 4,500,412 A | * | 2/1985 | Takahashi et al. | 204/425 |
| 7,458,206 B2 | * | 12/2008 | Yahata et al. | 60/297 |
| 7,726,187 B2 | * | 6/2010 | Sukegawa et al. | 73/204.27 |
| 7,779,626 B2 | * | 8/2010 | Ohsaki | 60/320 |
| 2001/0051108 A1 | | 12/2001 | Schonauer | |
| 2005/0154523 A1 | * | 7/2005 | Yahata et al. | 701/108 |
| 2006/0117737 A1 | * | 6/2006 | Ohsaki | 60/276 |
| 2007/0251315 A1 | * | 11/2007 | Sukegawa et al. | 73/204.27 |
| 2008/0190173 A1 | * | 8/2008 | Wienand et al. | 73/28.01 |
| 2008/0295590 A1 | * | 12/2008 | Sukegawa et al. | 73/204.26 |
| 2009/0051376 A1 | * | 2/2009 | Schnell et al. | 324/724 |
| 2009/0090622 A1 | | 4/2009 | Ripley | |

FOREIGN PATENT DOCUMENTS

| | | |
|---|---|---|
| AT | 501 386 B1 | 10/2008 |
| DE | 199 59 871 | 6/2001 |
| DE | 10 2004 028 997 | 1/2006 |
| DE | 10 20076 021 913 A1 | 11/2008 |
| WO | WO 2005/015192 A1 | 2/2005 |

* cited by examiner

*Primary Examiner* — Hezron E Williams
*Assistant Examiner* — Rodney T Frank
(74) *Attorney, Agent, or Firm* — Cozen O'Connor

(57) ABSTRACT

A method for on-vehicle functional diagnosis of a soot sensor and/or for detecting further components in the soot in a motor vehicle having an internal combustion engine, the soot sensor connected electrically to an evaluation circuit. To specify a method for functional diagnosis of a soot sensor and/or for detecting further components in the soot, by which it is possible to detect a faulty soot sensor and/or further components in the soot in an economical manner, the evaluation circuit measures a temperature coefficient of the soot sensor and detects the faultiness of the soot sensor and/or the presence of further components in the soot from the temperature coefficient of the soot sensor.

11 Claims, 3 Drawing Sheets

METHOD FOR THE ON-BOARD FUNCTIONAL DIAGNOSIS OF A SOOT SENSOR IN A MOTOR VEHICLE AND/OR FOR THE DETECTION OF FURTHER CONSTITUENTS IN THE SOOT

BACKGROUND OF THE INVENTION

1. Field of the Invention

The invention relates to a method for on-vehicle functional diagnosis of a soot sensor in a motor vehicle and/or for detecting further components in the soot, and to a soot sensor operated by this method, and to an evaluation circuit permanently installed in a motor vehicle having an internal combustion engine and intended for on-vehicle functional diagnosis of a soot sensor.

2. Description of the Related Art

There is currently a lot of discussion about the accumulation of pollutants from exhaust gases in the atmosphere. Along with this, the availability of fossil fuels is limited. One response to this is to thermodynamically optimize combustion processes in internal combustion engines to improve their efficiency. In the automotive sector, this is reflected in the increasing use of diesel engines. However, the disadvantage of this combustion technology relative to optimized spark-ignition engines is a significantly increased output of soot. The absorption of polycyclic aromatic compounds makes the soot highly carcinogenic, and there have already been various regulations in response thereto. Thus exhaust emissions standards incorporating upper limits for soot emissions have been issued. There is therefore a need to specify reasonably priced sensors which reliably measure the soot content of the exhaust gas stream in motor vehicles.

Soot sensors of this kind are used to measure the soot being emitted to ensure that the engine management system in a motor vehicle receives information in a current driving situation that enable it to reduce emission levels through adaptations by control measures. Soot sensors can be used to initiate active exhaust gas cleaning by exhaust gas soot filters or to bring about recirculation of the exhaust gas to the internal combustion engine. In the case of soot filtering, filters capable of being regenerated, which filter out a significant proportion of the soot content of the exhaust gas, are used. Soot sensors are required for the purpose of detecting soot, for monitoring the operation of the soot filters and for controlling the regeneration cycles of the latter.

For this purpose, a soot sensor can be fitted upstream and/or a soot sensor can be fitted downstream of the soot filter, which is also referred to as a diesel particulate filter.

The sensor fitted upstream of the diesel particulate filter serves to increase the reliability of the system and to ensure that the diesel particulate filter operates under optimum conditions. Since this depends very largely on the mass of soot deposited in the diesel particulate filter, accurate measurement of the concentration of particulates upstream of the diesel particulate filter system, especially determination of a high particulate concentration upstream of the diesel particulate filter, is very important.

A sensor arranged downstream of the diesel particulate filter makes it possible to perform on-vehicle diagnosis and furthermore serves to ensure correct operation of the exhaust gas aftertreatment system.

There have been various approaches to the detection of soot in the prior art. One approach, which is widely followed in laboratories, is to use the scattering of light by the soot particles. This approach is suitable for complex measuring instruments. Attempts to use this as a mobile sensor system in exhaust gas as well show that approaches that involve implementing an optical sensor in a motor vehicle are associated with high costs. There are furthermore unsolved problems with regard to the soiling of the optical windows by exhaust gases from combustion.

German Laid-Open Application DE 199 59 871 A1 discloses a sensor and an operating method for the sensor, based on thermal considerations. The sensor comprises an open porous molding, e.g. a honeycomb ceramic, a heating element and a temperature detector. When the sensor is brought into contact with a volume of gas to be measured, soot is deposited thereon. For measurement, the soot deposited within a particular period of time is ignited and burnt with the aid of the heating element. The increase in temperature, which occurs as it is burnt, is measured.

Among the known particle sensors for conductive particles are those in which two or more metallic electrodes are provided, said sensors having electrodes that intermesh in the manner of a comb. Soot particles that are deposited on these sensor structures short-circuit the electrodes and thus change the impedance of the electrode structure. As the concentration of particles on the sensor surface increases, a decreasing resistance and an increasing current at a constant applied voltage can thus be measured between the electrodes. A soot sensor of this kind is disclosed in DE 10 2004 028 997 A1, for example.

In general, the comb-type electrode structure of these soot sensors is formed by thin adjacent conductor tracks. The conductor tracks are 10 μm apart, for example. In addition to the desired change in the resistance of the soot sensor caused by soot loading of the comb structure, there may also be a change in the resistance of the soot sensor due to unwanted short circuits. These unwanted short circuits can be caused by electrodes that are scratched or partially detached, for example. The measured resistance of the soot sensor would be distorted by these unwanted short circuits, and this can only be detected by regular functional diagnosis of the soot sensor.

SUMMARY OF THE INVENTION

It is therefore an object of the invention to specify a method for functional diagnosis of a soot sensor and/or for detecting further components in the soot, by which it is possible to detect a faulty soot sensor and/or further components in the soot in an economical manner.

Regular monitoring of the soot sensor is possible by virtue of the fact that the soot sensor is connected electrically to an evaluation circuit, permanently installed in the motor vehicle. The evaluation circuit measures the temperature coefficient of the soot sensor and detects the faultiness of the soot sensor by the temperature coefficient. The motor vehicle does not have to be brought to a specialist service garage for the soot sensor to be monitored, yet the operation of the soot sensor can be monitored in an almost uninterrupted manner. Moreover, it is also possible for further components of the soot to be detected by the temperature coefficient of the soot sensor. If water, hydrocarbons, engine oil, abraded metallic material and/or ash components from burnt additives, for example, are present in the soot, this will result in a characteristic change in the temperature coefficient of the soot sensor. It is thus possible for the presence of such components in the soot to be detected by the temperature coefficient of the soot sensor.

In one embodiment of the invention, the evaluation circuit detects the faultiness of the soot sensor and/or the presence of further components in the soot if the temperature coefficient measured by the evaluation circuit is higher than that of a fault-free soot sensor.

The resistance of a substance is affected by changes in temperature. The flow of current itself produces energy conversion in the resistor. The directional motion of electrons in the electric current enters into interaction with the non-directional motion of all the particles in the resistor, which is described by Brownian molecular motion. As a result, the resistor heats up. As a consequence, the Brownian molecular motion increases and hinders the directional flow of current even more. Resistance increases as the temperature rises. This process can be observed in all metals. Metals are better electric conductors when cold. Thus metals are typical PTC resistors and PTC resistors have a positive temperature coefficient. Examples of the temperature coefficient α of some metals at 20° C. are:

Copper $\alpha=3.9 \cdot 10^{-3}$ $[K^{-1}]$
Silver $\alpha=3.8 \cdot 10^{-3}$ $[K^{-1}]$
Iron $\alpha=5.0 \cdot 10^{-3}$ $[K^{-1}]$
Platinum $\alpha=3.88 \cdot 10^{-3}$ $[K^{-1}]$ Carbon becomes a better conductor when heated than when cold. The bond between the valence electrons and the atomic nuclei is broken when thermal energy is supplied. This gives rise in each case to a free electron and a defect electron or electron hole. The electron hole carries a positive unit charge. The electron hole pair promotes current conduction when an electric voltage is applied. There is a dynamic equilibrium between pair formation and the re-combination thereof to give the uncharged atom. As the temperature rises, electron hole pair formation becomes easier and conductivity increases, i.e. resistance falls. Carbon and semiconductors are NTC resistors and have a negative temperature coefficient. At 20° C., carbon has the following temperature coefficient α, for example:

$$\alpha=-0.5 \cdot 10^{-3} \ [K^{-1}]$$

The measurement electrodes of the soot sensor have a comb structure with very small electrode spacings (e.g. 10 μm). If there is a short circuit in the electrode structure and the soot sensor is therefore faulty, there is a positive temperature coefficient since the conductivity is dominated by the current across the metallic short circuit.

If there is no metallic short circuit, and the soot sensor is therefore fault-free, the conductivity is dominated by the soot layer deposited on the electrodes. Soot consists primarily of carbon and is therefore a typical NTC resistor. If the soot sensor is intact, a negative temperature coefficient will therefore be found. It is thus easy to distinguish between a faulty and a fault-free soot sensor when the evaluation circuit measures a higher temperature coefficient than that of a fault-free soot sensor.

In one embodiment of the invention, the temperature coefficient of the fault-free soot sensor is stored in an electronic memory of the evaluation circuit. Electronic memories of this kind are very easy to produce on an integrated circuit. When a soot sensor that is as good as new and hence fault-free is first put into operation, the evaluation circuit can determine the temperature coefficient of the fault-free soot sensor and store it in the memory. As an alternative, the temperature coefficient of the fault-free soot sensor can be determined off the vehicle, before the soot sensor is fitted, and can be written externally to the electronic memory integrated into the evaluation circuit.

If the temperature coefficient of the soot sensor is measured with the internal combustion engine switched off, the result of measurement does not include any distortions due to fresh soot particles deposited during measurement.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

The present invention will be explained below by a preferred embodiment with reference to the accompanying drawings. This embodiment comprises a soot sensor for use in a motor vehicle. In the drawings.

DETAILED DESCRIPTION OF THE PRESENTLY PREFERRED EMBODIMENTS

Figure 1:
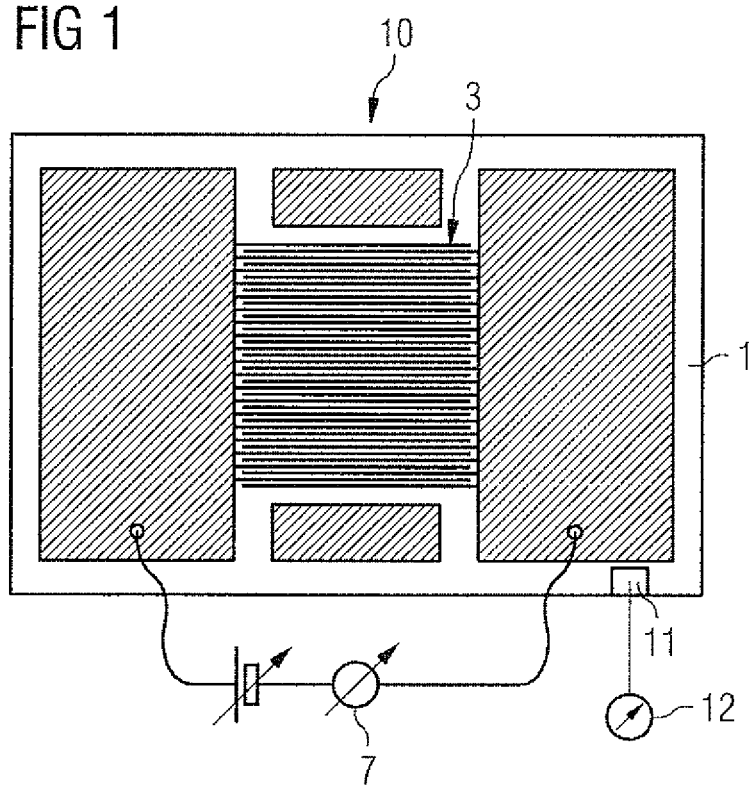
FIG. 1 is a soot sensor.

FIG. 1 shows a soot sensor 10, which is constructed from a molding 1, a heating element 2, and a structure consisting of measurement electrodes 3. The molding 1 can be produced from a ceramic material or from some other material that has electrically insulating properties and can easily withstand the burn-off temperature of soot. In order to burn off the soot from the soot sensor 10, the soot sensor 10 is typically heated to a temperature of between 500 and 800° C. by an electric resistance heater. The electrically insulating molding 1 must be able to withstand such temperatures without damage. Here, the structure of the measurement electrodes 3 is designed as a comb-type structure. An electrically insulating region of the molding 1 being visible between each two measurement electrodes 3. The flow of current from a voltage or current source between the electrode structures 3 is measured by a current measuring element 7. As long as the soot sensor 10 is completely free of soot particles 4, no direct current will be measurable by the current measuring element 7, since there is always a region of the molding 1 between the measurement electrodes 3 which has an electrically insulating effect and is not bridged by soot particles 4. FIG. 1 furthermore shows a temperature sensor 11 as a component part of the soot sensor 10 with an electronic temperature evaluation device 12 to monitor the temperature prevailing in the soot sensor 10, especially when the soot deposits on the soot sensor 10 are being burnt off.

Figure 2:
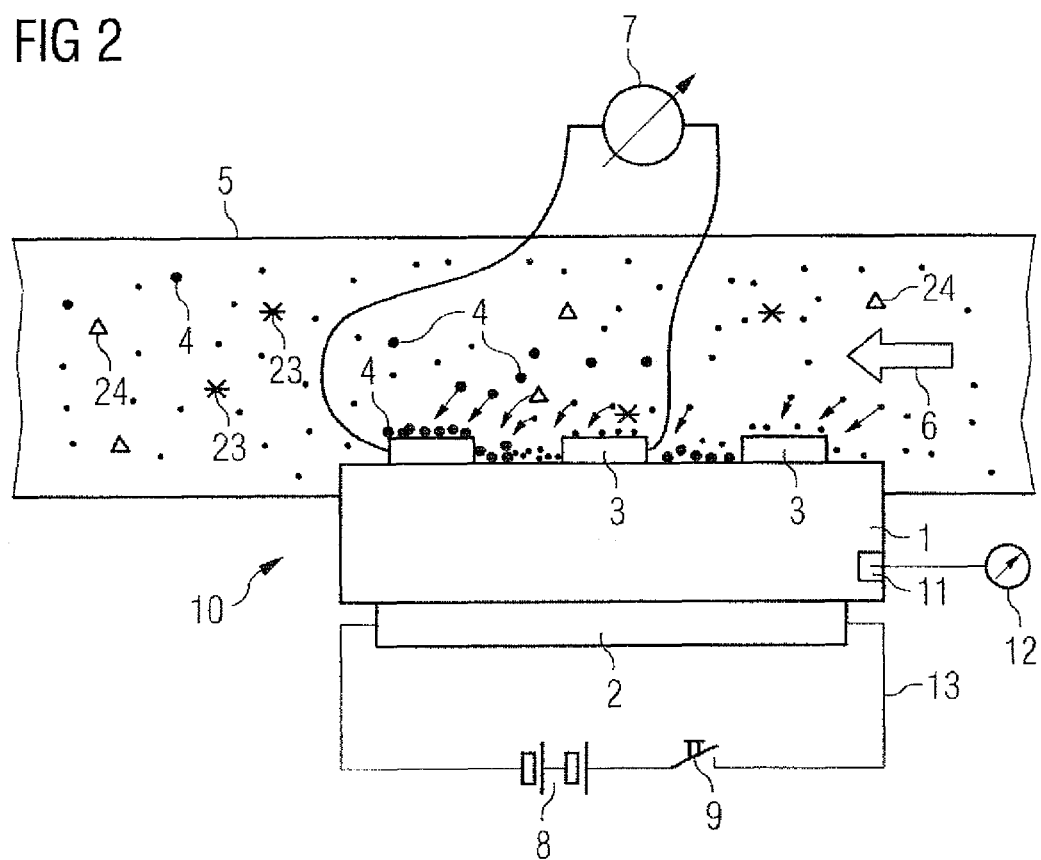
FIG. 2 is the soot sensor in operation.

FIG. 2 is the soot sensor 10 in operation. Here, the soot sensor 10 is arranged in an exhaust pipe 5, through which an exhaust gas stream 6 laden with soot particles 4 is passed. In addition to the soot particles 4, the exhaust gas stream 6 can also contain further components, such as water 23, hydrocarbons 24, engine oil and/or ash components from burnt additives. The direction of flow of the exhaust gas stream 6 is indicated by the arrow. It is then the function of the soot sensor 10 to measure the concentration of soot particles 4 in the exhaust gas stream 6. For this purpose, the soot sensor 10 is arranged in the exhaust pipe 5 in such a way that the structure comprising the measurement electrodes 3 faces or is exposed to the exhaust gas stream 6 and hence the soot particles 4. Soot particles 4 are deposited from the exhaust gas stream 6 both on the measurement electrodes 3 and on the insulating regions of the molding 1 in the spaces between the measurement electrodes 3. When enough soot particles 4 have been deposited on the insulating regions between the measurement electrodes 3, a direct current will flow between the measurement electrodes 3 due to the conductivity of the soot particles 4, and this current can be detected by the current measuring element 7. The soot particles thus bridge the electrically insulating spaces between the measurement electrodes 3. In this way, the concentration of soot particles 4 in the exhaust gas stream 6 can be measured with the soot sensor 10 shown here.

The soot sensor 10 in FIG. 2 furthermore exhibits the heating element 2, which can be supplied with electric current from the heating current supply 8 with the heating current circuit 13. In order to heat the soot sensor 10 to the burn-off temperature of the soot particles 4, the heating current switch 9 is closed, causing the heating element 2 to heat up and thus heating the entire soot sensor 10. Also integrated into the soot sensor 10 is the temperature sensor 11, which monitors the process of heating up the soot sensor 10 and hence the process of burning off the soot particles 4 by the electronic temperature evaluation device 12. The electric heating element 2 can be designed in such a way that it can be used simultaneously as a temperature sensor 11. The temperature coefficient can be determined easily by the electric heating element 2 and the temperature sensor 11, which is present on the soot sensor 10 in any case. It is therefore particularly economical to employ the method according to the invention since only the design features that are present on the soot sensor 10 in any case are used.

The temperature coefficient of the soot sensor 10 can, for example, be determined during each heating phase initiated for the purpose of burning soot off the electrode structure. However, it may also be expedient to employ a change in temperature that does not serve to regenerate the soot sensor to diagnose the soot sensor 10 for freedom from faults. Such a change in temperature can be caused solely by the change in the exhaust gas parameters or, alternatively, can be controlled by the heating element 2 without the soot being burnt off.

Here, the current measuring element 7, the electronic temperature evaluation device 12 and the heating current switch 9 are depicted as discrete components by way of example but, of course, these components can be part of a microelectronic circuit which is, for example, integrated into a control unit for the soot sensor 10.

Figure 3:
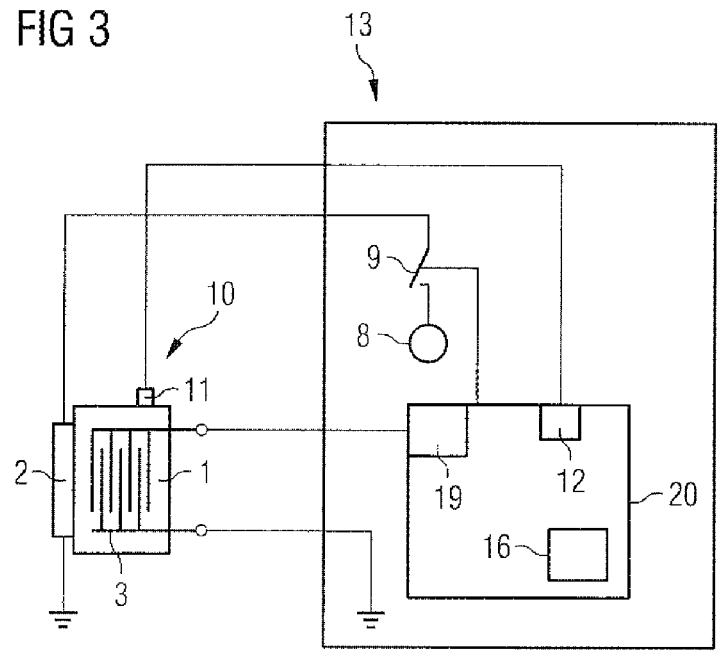
FIG. 3 is the evaluation circuit for on-vehicle functional diagnosis of the soot sensor permanently installed in a motor vehicle.

FIG. 3 is the evaluation circuit 13 for on-vehicle functional diagnosis of the soot sensor 10 and/or for detecting further components in the soot, said evaluation circuit being permanently installed in a motor vehicle 15. The soot sensor 10 has a measurement electrode structure which intermeshes in a finger-like manner and which does not have any metallic short circuits if the soot sensor 10 is intact. During measurement, soot particles 4 are deposited on and between the measurement electrodes 3, leading to a flow of current between the measurement electrodes 3. The current flow serving as a measure of the soot concentration in the exhaust gas stream 6. Above a certain quantity of soot particles 4 deposited on the measurement electrodes 3, however, a maximum conductivity across the soot layer is reached, and this cannot be increased further even if there is further deposition of soot. Above a certain quantity of deposited soot particles 4, the soot sensor 10 therefore goes "blind" regarding any further measurement of the soot concentration in the exhaust gas 6. It is then necessary to regenerate the soot sensor 10 by burning off the soot layer on the measurement electrodes 3. For this purpose, a heating current is passed from the heating current supply 8 to the heating element 2 by switching on the heating current switch 9. The soot sensor 10 is heated in a monitored way. The heating of the soot sensor is monitored by the temperature sensor 11 formed on or in the soot sensor 10. The dependence of the resistance of the soot sensor 10 or the conductivity of the latter (the conductivity corresponds to the reciprocal resistance) on the temperature at the soot sensor 10 can be recorded by the evaluation circuit 13. This forms the function of the resistance of the actual soot sensor 10 with respect to its temperature. The function of the resistance of a completely intact soot sensor 10 with respect to its temperature can be stored in the electronic memory 16. These functions describe the temperature coefficients of the actual soot sensor 10 and of the completely intact soot sensor 10. The significant difference in the temperature coefficients of intact and faulty soot sensors results from the fact that carbon and therefore soot is a typical NTC resistor and metallic conductors are typical PTC resistors. The function of the resistance of the soot sensor 10 with respect to its temperature and hence its temperature coefficient will depend significantly on whether a metallic conduction process or carbon/soot conduction is dominant. It is then possible to compare the measured temperature coefficient with that of an intact soot sensor 10 and to detect a faulty soot sensor 10 by this comparison.

The temperature coefficient describes a relative change in a physical variable as a function of the change in temperature with respect to a reference temperature. The temperature coefficient of a resistor indicates the change in the resistance of the resistor as a function of temperature and is shown in units of $K^{-1}$. The temperature coefficient is also referred to as a temperature factor of a resistor. For many resistor materials, especially metallic ones, this temperature coefficient is positive, with the result that higher resistance is encountered when the applied temperature is increased. In the case of the intact soot sensor 10, the temperature coefficient is negative because the resistance of the intact soot sensor 10 is due principally to the high electrical conductivity of the heated soot between the measurement electrodes 3. It should be stated clearly here that detection of the freedom of the soot sensor 10 from faults by measuring its temperature coefficient can make a significant contribution to monitoring of and compliance with the exhaust gas regulations in force.

In the evaluation circuit 13 on the microcontroller 20 there is an electronic memory 16, in which the temperature coefficient of a fault-free soot sensor 10 is stored. The measured temperature coefficient of the soot sensor 10 can then be compared with the temperature coefficient of a fault-free soot sensor 10, which is stored in the electronic memory 16. If the temperature coefficient of the soot sensor 10 measured by the evaluation circuit 13 is significantly higher than that of a fault-free soot sensor 10, the evaluation circuit 13 detects the faultiness of the soot sensor 10. A corresponding fault signal can then be sent to an engine management system in the motor vehicle, and the driver of the motor vehicle is requested to replace the soot sensor 10, and the fault is stored in the on-board diagnostic unit 22 of the motor vehicle.

Figure 4:
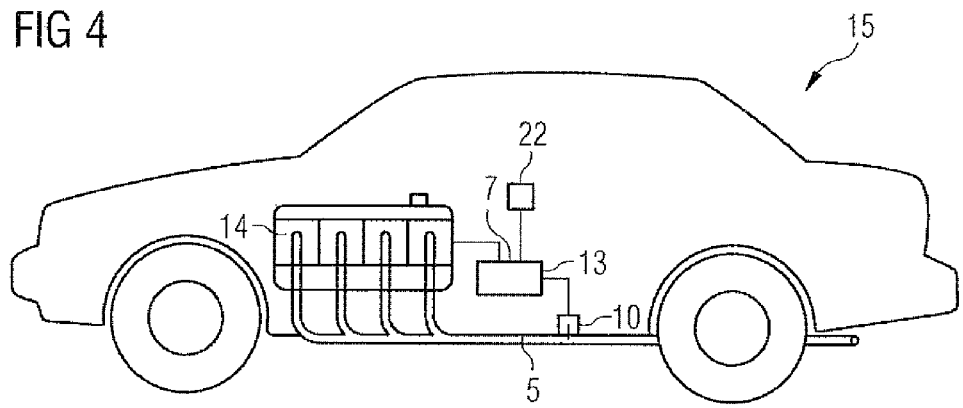
FIG. 4 is a motor vehicle having an internal combustion engine.

To give an overall illustration of the system as a whole, FIG. 4 shows a motor vehicle 15 having an internal combustion engine 14. The internal combustion engine 14 discharges the exhaust gas stream 6 produced by it via an exhaust pipe 5. Arranged in the exhaust pipe 5 is a soot sensor 10, which is connected to an evaluation circuit 13, which can also contain the current measuring element 7. The evaluation circuit 13 described in detail with reference to FIG. 3 transmits the signals on the faultiness of the soot sensor 10 and/or information obtained on further components of the soot to the on-board diagnostic unit 22. Both the current measuring element 7 for measuring the soot concentration of the exhaust gas stream 6 and the evaluation circuit 13 for on-vehicle functional diagnosis of a soot sensor 10 in a motor vehicle 15 can be constructed on one and the same integrated electronic circuit.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

We claim:

1. A method for at least one of on-vehicle functional diagnosis of a soot sensor and detecting further components in exhaust of an internal combustion engine, the soot sensor comprising:
   a substrate;
   a heating element configured to heat the substrate of the soot sensor;
   a temperature sensor configured to detect a temperature of the soot sensor;
   a structure arranged on the substrate comprising measurement electrodes configured as a comb-type electrode structure; and
   an evaluation circuit electrically coupled to the soot sensor, the method comprising:
   measuring a temperature coefficient of the soot sensor; and
   detecting, based on the temperature coefficient, at least one of:
      a defectiveness of the soot sensor and
      a presence of further components in the exhaust.

2. The method as claimed in claim 1, wherein the evaluation circuit detects the at least one of the defectiveness of the soot sensor and the presence of further components in the soot if the temperature coefficient measured by the evaluation circuit is higher than a temperature coefficient of a fault-free soot sensor.

3. The method as claimed in claim 2, further comprising storing the temperature coefficient of the fault-free soot sensor in a memory.

4. The method as claimed in claim 1, wherein the temperature coefficient of the soot sensor is measured with the internal combustion engine switched off.

5. A soot sensor comprising:
   a heating element configured to heat a substrate of the soot sensor;
   a temperature sensor configured to detect a temperature of the soot sensor;
   a structure arranged on the substrate comprising measurement electrodes configured as a comb-type electrode structure; and
   an evaluation circuit electrically coupled to the soot sensor, the evaluation circuit configured to:
      measure a temperature coefficient of the soot sensor; and
      detect, based on the temperature coefficient, at least one of:
         a defectiveness of the soot sensor and
         a presence of further components in the exhaust.

6. An evaluation circuit for on-vehicle functional diagnosis of a soot sensor permanently installed in a motor vehicle having an internal combustion engine, the evaluation circuit configured to at least one of functionally diagnose the soot sensor and detect further components in the soot, the soot sensor being electrically connected to the evaluation circuit, wherein the evaluation circuit is configured to:
   measure a temperature coefficient of the soot sensor and detect at least one of:
      a defectiveness of the soot sensor and
      further components in the soot from the temperature coefficient.

7. The evaluation circuit as claimed in claim 6, configured to compare the temperature coefficient measured by the evaluation circuit to a temperature coefficient of a fault-free soot sensor, wherein the evaluation circuit detects the at least one of the defectiveness of the soot sensor and the presence of further components in the soot if the temperature coefficient measured by the evaluation circuit is higher than the temperature coefficient fault-free soot sensor.

8. The evaluation circuit as claimed in claim 7, wherein the temperature coefficient of the fault-free soot sensor is stored in an electronic memory of the evaluation circuit.

9. The evaluation circuit as claimed in claim 6, wherein the temperature coefficient of the soot sensor is measured with the internal combustion engine switched off.

10. The evaluation circuit as claimed in claim 6, further comprising:
    a heating current supply configured to be coupled to a heating element of the soot sensor; and
    a heating current switch to couple the heating current to the heating element.

11. The method as claimed in claim 6, wherein the evaluation circuit is configured to detect the defectiveness of the soot sensor and the further components in the soot.

* * * * *